United States Patent [19]
Rutter

[11] Patent Number: 5,446,277
[45] Date of Patent: Aug. 29, 1995

[54] AUTOMATED LAMP MONITORING SYSTEM FOR COMPARING LIGHT INTENSITIES WITH A PRESELECTED VALVE

[76] Inventor: Robert E. Rutter, 40 Placitas Trails Rd., Placitas, N. Mex. 87043

[21] Appl. No.: 173,087

[22] Filed: Dec. 27, 1993

[51] Int. Cl.6 .................................................. H01J 40/14
[52] U.S. Cl. .................................. 250/214 R; 356/151
[58] Field of Search .............. 250/227.31, 205, 214 R; 356/213, 215, 224; 315/149, 150, 151

[56] References Cited

U.S. PATENT DOCUMENTS

| | | | |
|---|---|---|---|
| 3,366,835 | 1/1968 | Morris | 315/134 |
| 3,541,504 | 11/1970 | Bush | 340/52 |
| 3,588,816 | 6/1971 | Raymond | 340/80 |
| 3,609,450 | 9/1971 | Hart | 315/82 |
| 3,624,629 | 11/1971 | Donaldson | 340/251 |
| 3,634,694 | 1/1972 | Hardesty et al. | 250/217 |
| 4,227,808 | 10/1980 | Yuasa | 356/218 |
| 4,376,910 | 3/1983 | Peslier | 315/134 |
| 4,572,987 | 2/1986 | Embrey et al. | 315/77 |
| 4,982,139 | 1/1991 | Amir et al. | 315/151 |
| 4,994,845 | 2/1991 | Naruse et al. | 354/415 |
| 5,105,124 | 4/1992 | Futsuhara et al. | 315/129 |
| 5,235,252 | 8/1993 | Blake | 315/151 |

OTHER PUBLICATIONS

Henderson, Breck W., "FAA: Aircraft Strobe Lights May Fall Short of Standards", *Aviation Week & Space Technology*, pp. 42–43, Sep. 14, 1992.
Gradov, V. M., et al., "Theory of Powerful Nonsteady Xenon Discharge Taking Vaporization of its Stabilizing Walls Into Account", translated from *Teplofizika Vysokikh Temperatur*, vol. 19, No. 1, pp. 28–35, Jan.–Feb. 1981.

*Primary Examiner*—David C. Nelms
*Assistant Examiner*—Steven L. Nichols
*Attorney, Agent, or Firm*—DeWitt M. Morgan; Kevin Lynn Wildenstein

[57] ABSTRACT

Flash tube and lamp monitoring systems. The flash tube intensity monitoring system includes: a human eye spectral response photodiode for producing analog signals, each of which is directly proportional to the intensity of each flash from the flash tube; electronics for converting each of the analog signals to a digital time function proportional to the intensity of the corresponding flash; and electronics, including a microprocessor, for monitoring each of the digital time functions, for flagging those time functions which are below a preselected minimum, and for sending a fault signal when a preselected number of consecutive time functions are below the pre-selected minimum. The monitoring system and flash tube are, preferably, incorporated into single unit for easy installation in the fuselage of an aircraft. The lamp monitoring system includes: a light pickup; a photodiode for producing an analog signal which is directly proportional to the intensity of the lamp being monitored; a line transceiver; an A/D converter; and a microcontroller. The microcontroller, which has a unique identification code, sends a command to the A/D converter only upon receipt of the matching poll command.

18 Claims, 7 Drawing Sheets

AUTOMATED LAMP MONITORING SYSTEM FOR COMPARING LIGHT INTENSITIES WITH A PRESELECTED VALVE

FIELD OF THE INVENTION

This invention relates to systems for the automatic self monitoring of the intensity of illumination sources, such as aircraft anti-collision flash tubes and incandescent lamps used in airport approach lighting systems, and the sending of a fault signal to a monitoring system when the illumination falls below a predetermined level.

BACKGROUND OF THE INVENTION

Xenon flash tubes are mandated for use as anti-collision lights on aircraft. These tubes produce sudden, brilliant flashes of light that are much more conspicuous than other light sources. Current FAA (i.e., Federal Aviation Administration) mandated airworthiness standards require that such flash tubes have an effective intensity of 400 candela when viewed within 5 degrees of horizontal for aircraft certified after 1977. For aircraft certified before 1977 the requirement is 100 candela.

In a new strobe unit, the intensity of the xenon flash tube will meet or exceed FAA brightness standards. However, the intensity significantly degrades with use, long prior to actual tube failure. See: B. W. Henderson, "FAA: Aircraft Strobe Lights May Fall Short of Standards" *Aviation Week & Space Technology*, pp 42–43, Sep. 14, 1992; and V. M. Gardov, et al., "Theory of Powerful Nonsteady Xenon Discharge Taking Vaporization of Its Stabilizing Walls Into Account" translated from *Teplofizika Vysokikh Temperatur*, Vol. 19, No. 1., pp. 28–35, January-February, 1981. The result is that most flash tubes continue to work long after they have degraded below FAA minimum brightness requirements. An FAA survey showed that airlines generally rely on the technical manuals from the strobe light suppliers, which do not recommend checking brightness or regularly replacing xenon flash tubes. See Henderson, supra.

Strotek (Carson City, Nev.) claims to have developed a portable optical measuring system which can check flash tube intensity from outside the aircraft while they are on the ground. However, such a system is not an automatic self monitoring system, as disclosed and claimed herein.

U.S. Pat. No. 3,366,835 to H. L. Morris discloses a circuit for indicating a flash tube failure when the monitored tube is located where it is not readily visible to the operator. The failure indicator includes a light conducting plastic rod 48 which extends from the vicinity of the flash tube 14 to a photocell 49. Photocell 49 is part of a circuit including relay 53, capacitor 54, contacts 55 and warning light 56. If the flash tube fails to light for a predetermined period, capacitor 54 does not recharge and relay 53 is de-energized. Contact 55 then closes and the indicator light 56 comes on.

A similar problem is encountered with airport runway approach lighting systems. PAR-38 and PAR-56 tungsten-halogen incandescent lamps are currently used. The FAA requires that all lamps in a given system be of even brightness. However, the PAR lamps age with use, with the unacceptable result that some lamps appear dimmer than others.

A common solution to the foregoing problem with approach lighting systems is, per FAA regulations, to replace all the lamps in the system on a periodic basis (e.g., every 400 hours at major airports) even though many of the lamps still meet illumination requirements. Alternately, indirect monitoring systems are used which are subject to false indications caused by variances in loop current and lamp impedance, aging effects and by shorting devices intended to protect the system when a lamp fails. U.S. Pat. No. 5,105,124 to K. Futsuhara, et al., discloses a system in which a feedback signal consisting of a unique frequency for each lamp flows through the lamp circuit. Thus, any failed lamp can be detected by checking this feedback signal. Unfortunately, this system does not detect lamps which have not failed, but are below FAA brightness requirements.

Numerous other lamp failure indicators are disclosed in the prior art. See, for instance: U.S. Pat. No. 3,541,504 to R. H. Bush, which is described as a vehicle burn-out indicator; U.S. Pat. No. 3,588,816 to R. H. Himes; U.S. Pat. No. 3,624,629 to C. A. Donaldson; U.S. Pat. No. 4,572,987 to D. M. Embrey, et al.; and U.S. Pat. No. 4,376,910 to J.P. Pieslier.

In view of the foregoing, it is an object of the present invention to provide systems for the continuous monitoring of flash tubes and continuous illumination sources, which systems provide a fault signal or other indication when the intensity of the source being monitored falls below a predetermined (sometimes mandated) value (e.g., a minimum set by a regulatory agency such as the FAA).

It is also an objection of the invention to improve airport runway approach lighting by providing a system capable of monitoring, either continuously or on command, each of the lamps used therein and providing a fault signal or other indication when the intensity falls below the required minimum (even though the lamp has not failed).

It is a further object of the invention to use the existing runway approach lamp power grid to avoid the requirement for any additional wiring.

It is another object of the invention to provide a system which can be used to monitor both high intensity constant current and medium intensity constant voltage runway approach lighting systems.

The foregoing improves both aircraft and runway safety and, at least in the case of runway approach lights, reduces the unnecessary replacement of lights in those systems where, for lack of applicant's monitoring system, all lamps are replaced on a periodic basis regardless of their individual intensities. In addition, the monitoring capability can statistically record average bulb lifetimes, thus allowing an accurate forecasting of bulb purchases.

SUMMARY OF THE INVENTION

A flash tube intensity monitoring system including: a human eye spectral response photodiode for producing analog signals, each of which is directly proportional to the intensity of each flash from the flash tube; electronics for converting each of the analog signals to a digital time function proportional to the intensity of the corresponding flash; and electronics, including a microprocessor, for monitoring each of the digital time functions, for flagging those time functions which are below a preselected minimum, and for sending a fault signal when a preselected number of consecutive time functions are below the pre-selected minimum. The monitoring system and flash tube are, preferably, incorporated into single unit for easy installation in the fuselage of an aircraft. The unit includes structure, interposed between the flash tube and the photodiode for at least partially blocking heat from the flash tube from reaching the photodiode. The unit also includes a light pipe which samples the light from the flash tube and transmits this sampled light to the photodiode. The electronics for converting the analog signals includes an analog integration circuit and a calibration circuit. The microprocessor looks for variations in flash intensity as seen by the photodiode.

The lamp monitoring system, for incandescent or other continuous light sources, includes a light pickup, a photodiode for producing an analog signal which is directly proportional to the intensity of the lamp being monitored, a line transceiver for sending and receiving digital data and instructions over the lamp's power line, means for converting the analog signals to a digital function proportional to the intensity of the lamp, and a microcontroller connected to the line transceiver and the converting means. The converting means is connected to the photodiode and the line transceiver. The microcontroller includes a unique identification code and is adapted to receive a poll command over the power line, whereby when the microcontroller receives the poll command which matches the unique identification code it sends a command to the converting means and the converting means converts the analog signals to said digital function. The monitoring system also includes apparatus for amplifying and conditioning the analog signals from the photodiode so as to fit the input range of the converting means (preferably an A/D chip). The monitoring system further includes an optical pickup bezel for collecting visible light from the lamp, which bezel contacts at least a portion of the perimeter of the lamp without degrading or interfering with the lamp's projected beam path. The monitoring system also further includes an optical coupling which separates the photodiode, the line transceiver, A/D chip, and microcontroller from the intense heat generated by the lamp.

DESCRIPTION OF THE PREFERRED EMBODIMENT

Figure 1:
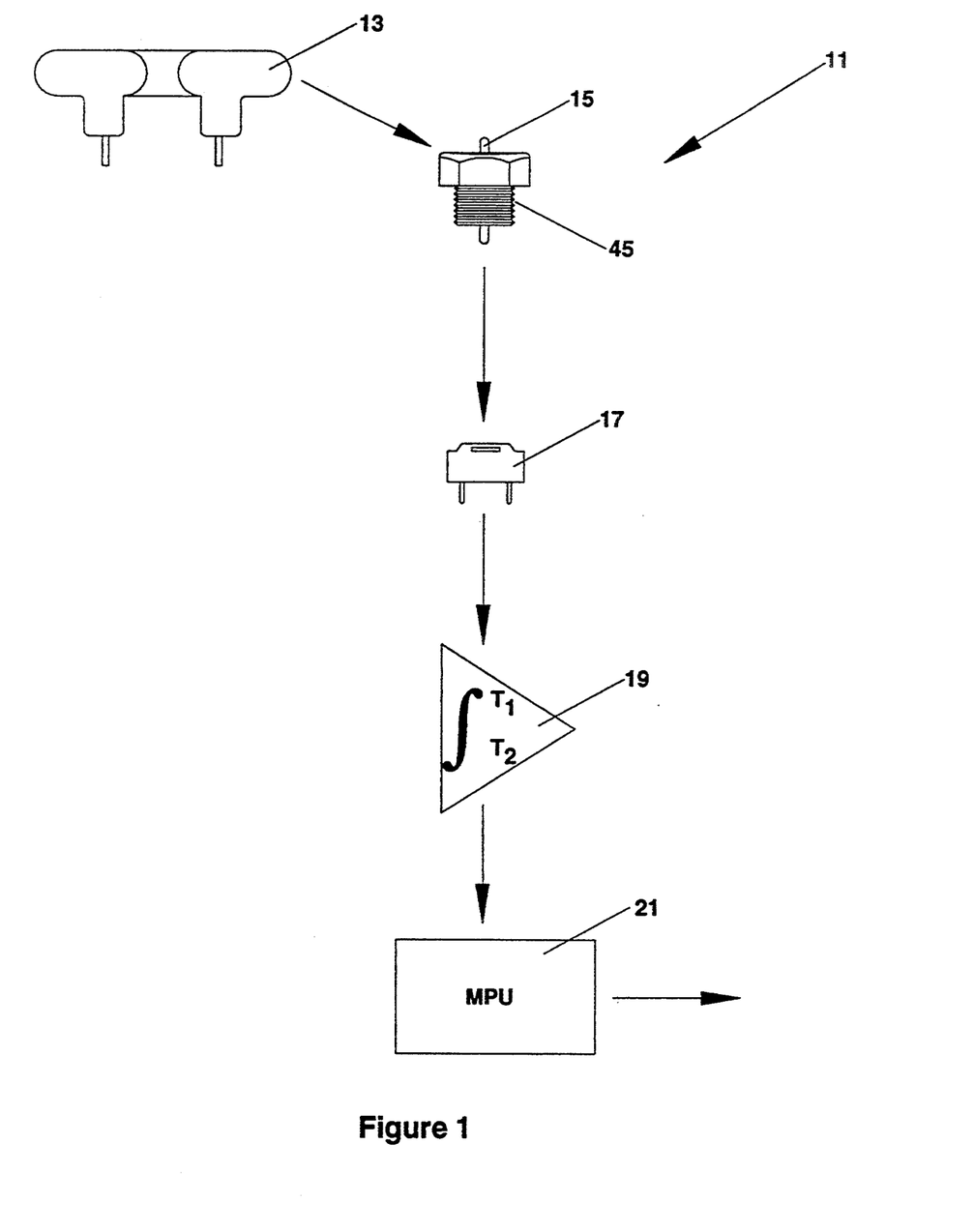
FIG. 1 is a block diagram of the preferred embodiment of the flash intensity self monitoring system of the present invention.

With referenced to FIG. 1, flash intensity self monitoring system 11 includes an anti-collision light flash tube 13 (such as a made by Grimes, Hella and Flight Components), a light pipe 15, a photodiode 17, an optic board 19 (for the integration and conversion of analog electric signals to a digital time function), and a microcontroller 21. Light pipe 15 is, preferably, made of pyrex or other suitable light transmitting material. For the reasons set forth below, each end of light pipe 15 is hemispheric. For aircraft anti-collision flash tubes, the photodiode 17 is a human eye spectral response photodiode.

Figure 2:
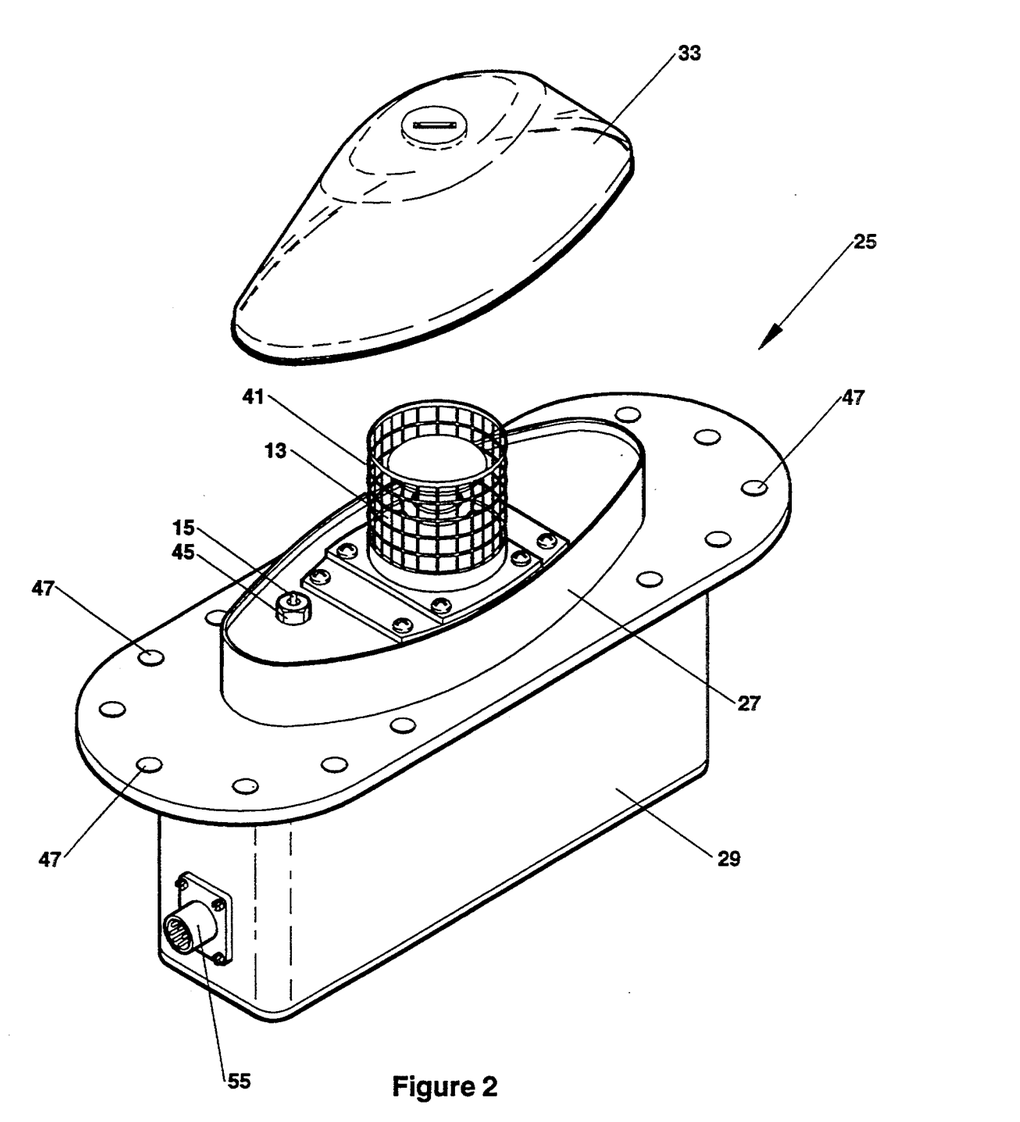
FIG. 2 is a perspective view of the flash tube housing of the preferred embodiment.
Figure 3:
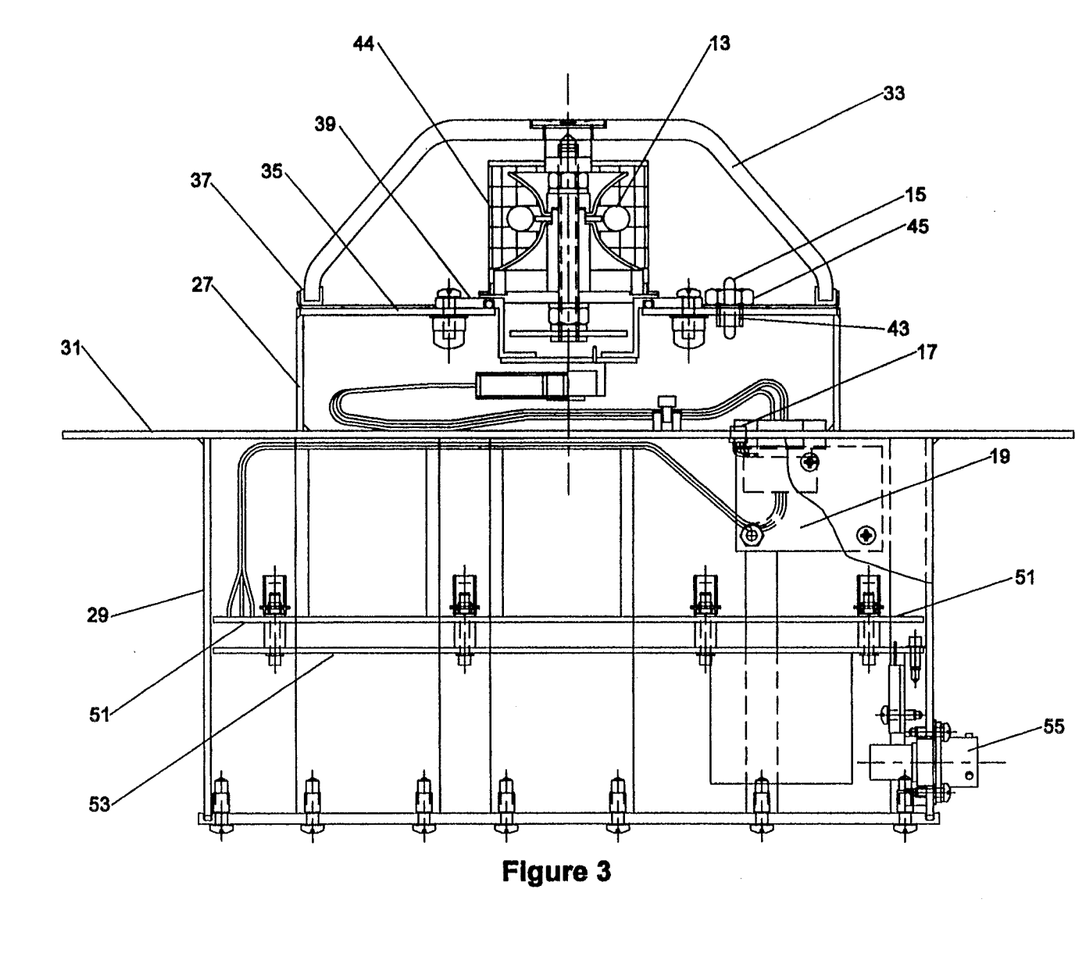
FIG. 3 is a sectional view of the flash tube housing of FIG. 2.

The above-identified components are housed in anti-collision light unit 25, as illustrated in FIGS. 2 and 3. Unit 25 includes an external housing 27, an internal housing 29, a fuselage mounting plate 31, and a glass flash tube cover 33. External housing 27 includes a flash tube unit mounting plate 35, and a gasket 37. The flash tube unit includes a mounting plate 39, a shield 41, conventional mechanical apparatus (not shown) for attaching cover 33 and conventional flash tube electrical connectors (also not shown). Flash tube mounting plate 35 includes an opening 43 (see FIG. 3) for supporting light pipe adaptor 45. Plate 31 includes a plurality of mounting holes, such as illustrated at 47, to secure unit 25 to the fuselage of an aircraft, and an opening (not shown) for supporting the sensor portion of photodiode 17 within housing 27 and beneath light pipe 15. Diode 17 does not have to be aligned with light pipe 15. Housing 29 supports optic board 19 and MPU board 51 (which includes microcontroller 21), circuit board 53 (of conventional design, for energizing flash tube 13), and conventional electric connector 55.

Electrical wiring (partially shown) interconnects the various boards and electrical components. Light pipe 15 is positioned laterally from flash tube 13 and photodiode 17 is positioned below plate 35 a distance sufficient to prevent photodiode 17 from being adversely affected by the intense heat generated by flash tube 13. The end of light pipe 15 exposed to flash tube 13 is rounded so that there is no alignment requirement when it is screwed into place. The opposite end is also rounded to provide diffused light. The use of such diffused light attenuates the intensity of the light from flash tube 13 on photodiode 17, to a level below that which would overdrive or saturate photodiode 17.

Figure 4:
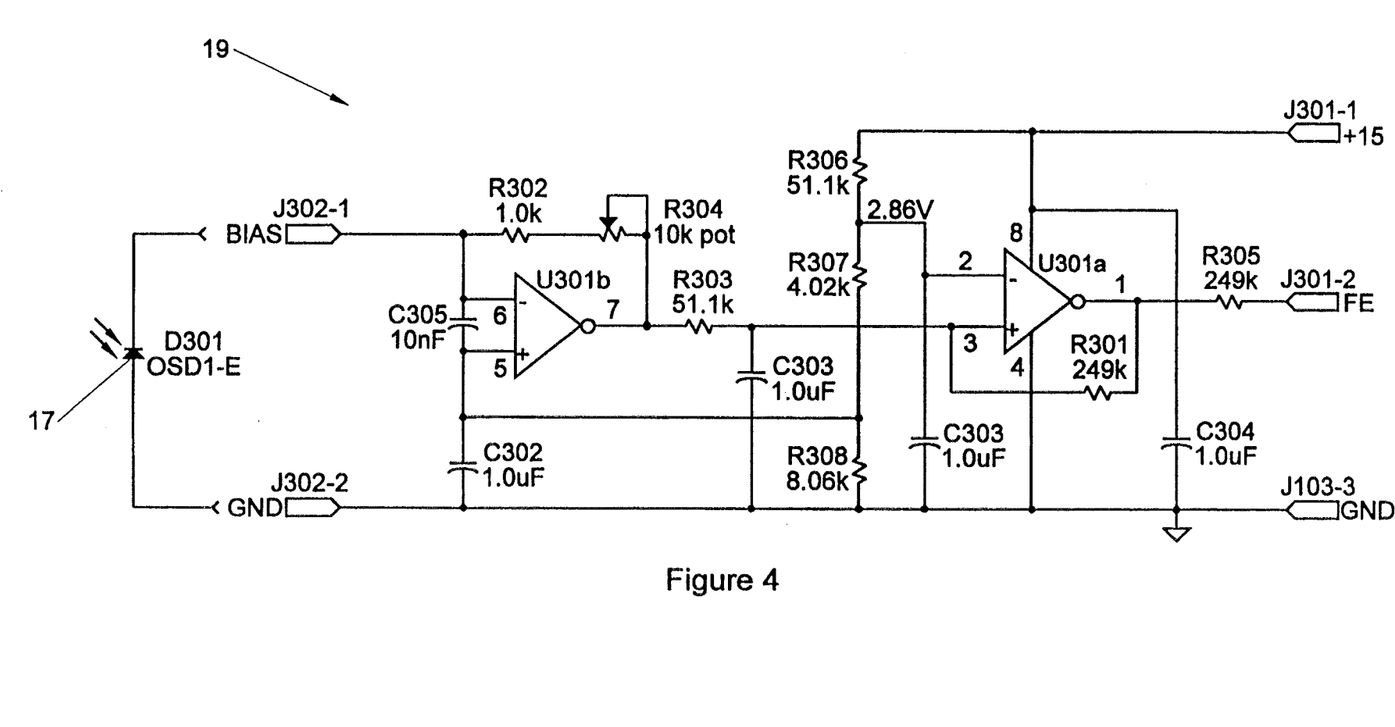
FIG. 4 is an electrical schematic of the optic board of the present invention.

The design of optic board 19 and MPU board 51 could, as those skilled in the art will appreciate, take a number of forms. As illustrated schematically in FIG. 4, optic board 19 is powered from the regulated +15 volts coming in through pin 1 of J301. Resistors R306, R307 and R308 are used to create a reference voltage of 5 volts and a bias voltage of 3 volts. The 3 volt bias voltage is applied across photodiode 17 by op amp B of U301. This bias voltage is necessary to speed up the response time of photodiode 17. Potentiometer R304 is used to adjust the gain of op amp B of U301. Due to normal manufacturing tolerances, there will be variations in the optical light path between flash tube 13 and photodiode 17. This will cause variations in the light intensity of the strobe flash as seen by the photodiode. There will also be slight variations in the photodiode's sensitivity. Gain potentiometer R304 is used to calibrate the optic board and to correct for any differences in the optical path. Resistor R303 and capacitor C301 form the analog integration network. Op amp A of U301, wired as an comparator to the 5 volt reference, changes this analog signal from C301 to a time function binary signal which is output through R305. This signal goes off the board through pin 2 of J301 and goes directly to microcontroller 21.

Figure 5A:
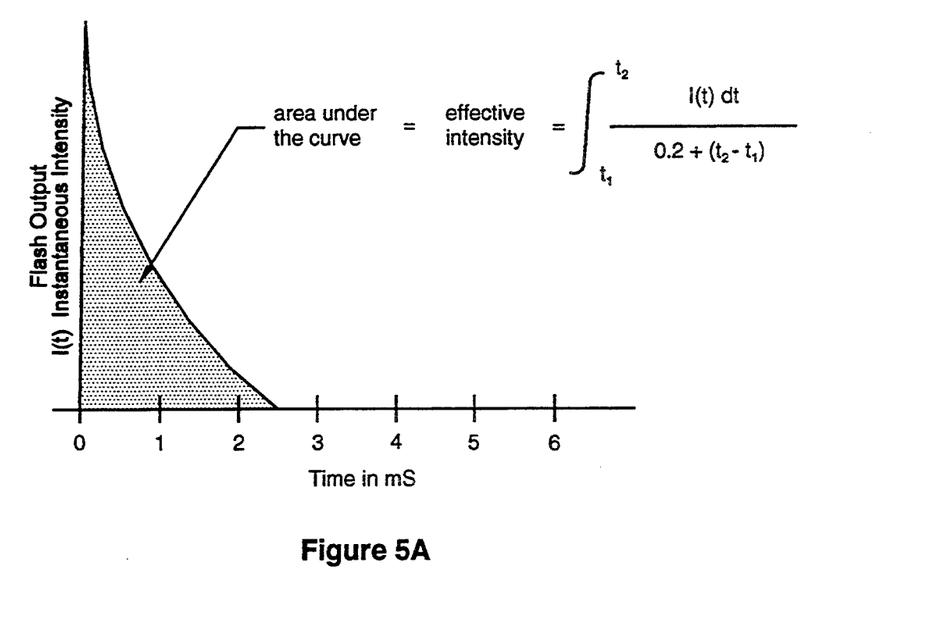
FIG. 5A is a timing diagram illustrating flash output v. time (in mS) for the flash tube.
Figure 5B:
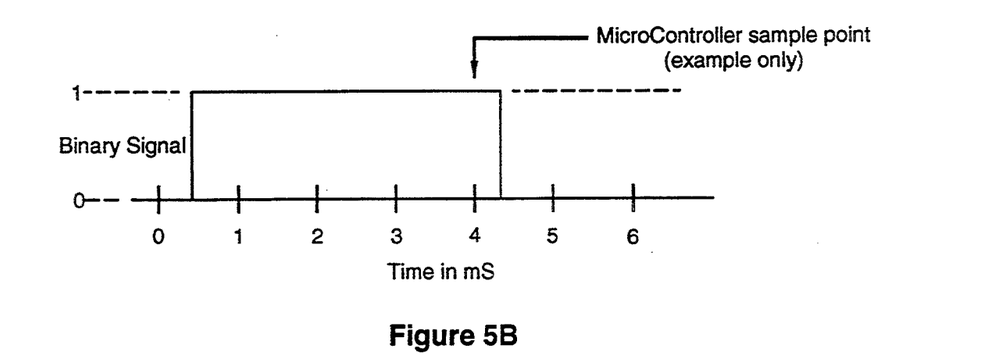
FIG. 5B is the timing diagram for the binary signal from the optic board v. time (in mS)

In operation, flash tube 13 is energized via conventional electronics such as located on board 53 (not shown). A portion of the light emitted from each flash is transmitted, via light pipe 15, to photodiode 17 which, in turn, sends an analog signal to optics board 19. The effective intensity of a strobe light is defined as an integral of the instantaneous intensity taken over the flash duration. With reference to FIGS. 5A and 5B, the analog signal from photodiode 17 is integrated and converted into a digital time function. Specifically, the analog signal is integrated by optic board 19 into a binary function in which the time duration of the binary signal represents the effective intensity of the flash. Microcontroller 21 samples the binary signal after each flash at a predetermined point (as indicated in FIG. 5B). If the flash intensity is above the acceptable intensity (e.g., at or above 400 candela), microcontroller 21 will see a binary 1. If the flash intensity falls below the required minimum, microcontroller 21 will see a binary 0. Repeated flashes (e.g. 250; 50 flashes per minute for 5 minutes) at output levels below the predetermined minimum will cause microcontroller to send a fault signal indicating that flash tube 13 should be replaced.

Figure 6:
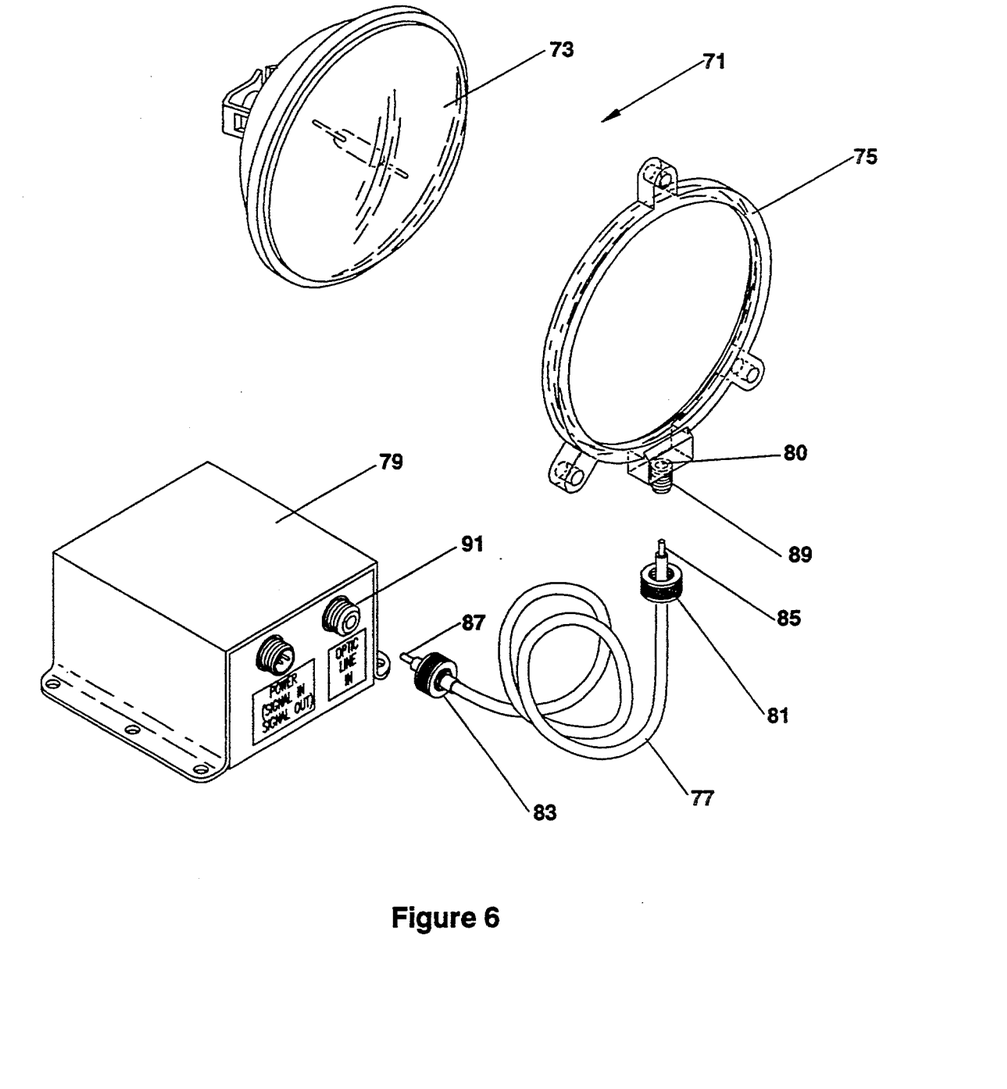
FIG. 6 is a perspective view of the major components of the automatic incandescent lamp monitoring system of the present invention.

With reference to FIG. 6, the major components of an automatic incandescent lamp monitoring system 71 for, for instance, airport runway approach lighting systems, is illustrated. System 71 includes a plurality of approach lamps 73 (typically PAR-56 or PAR-38 lamps), each of which includes an optical pickup bezel 75, fiber optic line 77, and monitor module 79. Bezel 75 is made of pyrex or other similar material to pick up light from around the entire perimeter of lamp 73, without degrading or interfering with the lamp's projected beam path. By internal reflection a portion of the light picked up is directed to pick up point 80. Line 77 includes standard couplers 81, 83 and exposed fiber ends 85, 87. Coupler 81 mates with threaded adaptor 89 to position end 85 within bezel 75 at pick-up point 80. Coupler 83 mates with threaded adaptor 91 to position tip 87 within the housing of monitor module 79.

Figure 7:
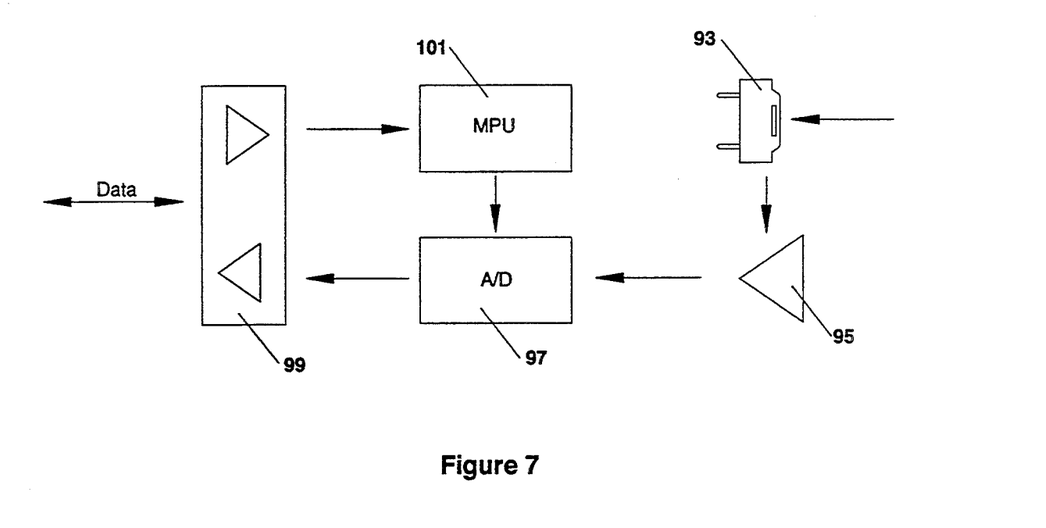
FIG. 7 is a block diagram of the lamp monitoring module of FIG. 6.

The basic internal components of module 79, which are illustrated in FIG. 7, include a photodiode 93, a signal conditioning stage 95, and A/D converter 97, a power line transceiver 99, and a microcontroller 101. Photodiode 93 is a human eye spectral response photodiode. Signal conditioning stage 95 amplifies and conditions the analog signal from photodiode 93 so that it fits the input range of A/D converter 97. The conditioning includes calibration and temperature compensation circuits. A/D converter 97 may be a serial output 5.6$\mu s$ 12-bit A/D converter such as the Maxim Max 170. A/D converter 97 only reads the signal from conditioning stage 95 in response to a command from microcontroller 101. Transceiver 99 may be a commercial grade FM line transmitter/receiver unit, which includes a transformer to electronically couple the components of module 79 to the power line (not shown) for lamp 73. This permits the lamp monitoring system to send the digital information along the power lines which have already been put in place to run the lamps being monitored. Finally, MPU 101 is, preferably, a single chip programmable microcontroller such as a PIC16C56.

In operation, each MPU 101 is programmed to respond only to a unique poll command. A master computer (not shown) at a remote location monitors all lamps in the array by polling each lamp (in sequence or as otherwise directed). When MPU 101 receives its unique poll command, via the associated lamp's power line, it commands A/D converter 97 to function. In response to this command, A/D converter 97 reads the voltage signal from conditioner 95, converts this signal to a 12 bit digital word, which is then output to transceiver 99. Transceiver 99 then sends the digital signal over the power line of lamp 73 to the master computer which processes the signal with a lookup table or equivalent to determine if the brightness of lamp 73 is within range.

Whereas the drawings and accompanying description have shown and described the preferred embodiment of the present invention, it should be apparent to those skilled in the art that various changes may be made in the form of the invention without affecting the scope thereof.

I claim:

1. A flash tube intensity monitoring system, said system comprising:
   a. a human eye spectral response photodiode for producing analog signals, each of said analog signals being directly proportional to the intensity of each flash from said flash tube;
   b. means for converting each of said analog signals to a digital time function proportional to said intensity of the corresponding one of said flash; and
   c. means for monitoring each of said digital time functions, for flagging those of said time functions which are below a preselected minimum and for sending a fault signal when a preselected number of consecutive time functions are below said preselected minimum.

2. The monitoring system as set forth in claim 1, further including means, interposed between said flash tube and said photodiode, for at least partially blocking infrared radiation from reaching said photodiode.

3. The monitoring system as set forth in claim 2, wherein said means for blocking is a light pipe which filters infrared radiation.

4. The monitoring system as set forth in claim 1, wherein said means for converting said analog signals includes analog integration on circuit.

5. The monitoring system as set forth in claim 4, wherein said analog integration circuit includes a resistor, a capacitor and an operational amplifier.

6. The monitoring system as set forth in claim 1, wherein said means for converting includes means to compensate for variations in said flash intensity from said flash tube as seen by said photodiode.

7. The monitoring system as set forth in claim 1, wherein said means for monitoring includes a microcontroller.

8. An automated anticollision light monitoring unit for aircraft, said unit comprising:
   a. a housing;
   b. a flash tube supported by said housing;
   c. a human eye spectral response photodiode disposed relative to said housing, said diode producing an electronic signal, said signal being proportional to the intensity of the corresponding flash from said flash tube;
   d. means for converting said electronic signal to a digital time function proportional to said intensity of said corresponding flash; and
   e. means for monitoring said digital function and for generating a fault signal when said digital function is below a preselected value for a preselected period of time, said converting means interconnecting said monitoring means and said photodiode.

9. The unit as set forth in claim 8, further including means for shielding said photodiode from the heat generated by said flash tube.

10. The unit as set forth in claim 9, further including means, interposed between said flash tube and said photodiode for at least partially blocking infrared radiation from reaching said photodiode.

11. A monitoring system for a lamp such as used in an airport approach array, said lamp having a power line, said system comprising:
   a. a light pickup positionable relative to said lamp to pick up a portion of the light emitted by said lamp;
   b. a human eye spectral response photodiode for producing an electronic signal which is proportional to the intensity of visible light emitted by said lamp;
   c. a line transceiver for sending and receiving digital data and instructions over said lamp power line;
   d. means for converting said electronic signal to a digital function proportional to the intensity of said lamp, said converting means connected to said photodiode and said line transceiver; and
   e. a microcontroller connected to said line transceiver and said converting means, said microcontroller including a unique identification code and adapted to receive a poll command over said power line, whereby when said microcontroller receives a poll command which matches said unique identification code, said microcontroller sends a command to said converting means and said converting means converts said electronic signal to said digital function.

12. The monitoring system as set forth in claim 11, further including means for amplifying and conditioning said electronic signal from said photodiode so as to fit the input range of said converting means.

13. The monitoring system as set forth in claim 12, wherein said converting means is an A/D chip.

14. The monitoring system as set forth in claim 11, further including an optical pickup bezel for collecting visible light from said lamp for transmission to said photodiode.

15. The monitoring system as set forth in claim 14, wherein said bezel contacts at least a portion of the perimeter of said lamp without degrading or interfering with said lamp's projected beam path.

16. The monitoring system as set forth in claim 14, further including optical coupling means for coupling said bezel to said photodiode.

17. The monitoring system as set forth in claim 16, wherein said optical coupling means separates said photodiode, said line transceiver, said converting means, and said microcontroller from the intense heat generated by said lamp.

18. The monitoring system as set forth in claim 17, wherein said optical coupling means is a fiber optic cable.

* * * * *